(12) United States Patent
Schober et al.

(10) Patent No.: US 10,202,495 B2
(45) Date of Patent: Feb. 12, 2019

(54) ENZYMATICALLY MODIFIED LIGNINS

(71) Applicants: SIKA TECHNOLOGY AG, Baar (CH); EMPA, Dübendorf (CH)

(72) Inventors: Irene Schober, Zurich (CH); Michael Richter, Straubing (DE); Tobias Heck, Bern (CH); Dagmara Jankowska, St. Gallen (CH)

(73) Assignees: SIKA TECHNOLOGY AG, Baar (CH); EMPA, Dubendorf (CH)

( * ) Notice: Subject to any disclaimer, the term of this patent is extended or adjusted under 35 U.S.C. 154(b) by 7 days.

(21) Appl. No.: 15/459,459

(22) Filed: Mar. 15, 2017

(65) Prior Publication Data

US 2017/0267816 A1 Sep. 21, 2017

(30) Foreign Application Priority Data

Mar. 15, 2016 (EP) .................................... 16160521

(51) Int. Cl.
| | | |
|---|---|---|
| C08H 7/00 | (2011.01) | |
| C04B 24/24 | (2006.01) | |
| C12P 7/22 | (2006.01) | |
| C04B 24/18 | (2006.01) | |
| C12P 19/04 | (2006.01) | |
| C04B 103/30 | (2006.01) | |
| C04B 103/40 | (2006.01) | |

(52) U.S. Cl.
CPC ............... C08H 6/00 (2013.01); C04B 24/18 (2013.01); C04B 24/24 (2013.01); C12P 7/22 (2013.01); C12P 19/04 (2013.01); C12Y 110/03002 (2013.01); C04B 2103/30 (2013.01); C04B 2103/408 (2013.01)

(58) Field of Classification Search
CPC .................... C04B 24/18; C08H 6/00
See application file for complete search history.

(56) References Cited

U.S. PATENT DOCUMENTS

| | | | |
|---|---|---|---|
| 4,703,801 A | | 11/1987 | Fry et al. |
| 4,892,588 A | * | 1/1990 | Dilling ..................... C08H 6/00 106/501.1 |
| 5,608,040 A | | 3/1997 | Huttermann et al. |

FOREIGN PATENT DOCUMENTS

| | | |
|---|---|---|
| EP | 0367389 A1 | 5/1990 |
| EP | 1040145 B1 | 4/2004 |
| WO | 95/08588 A1 | 3/1995 |

OTHER PUBLICATIONS

Ibrahim et al, laccase catalysed modification of lignin subunits and coupling to p-aminobenoic acid, journal of molecular catalysis B: enzymatic, 97, pp. 45-53 (Year: 2013).*
Aug. 26, 2016 Written Opinion and Search Report issued in Patent Application No. 16160521.7.

* cited by examiner

*Primary Examiner* — Melvin C. Mayes
*Assistant Examiner* — Stefanie J Cohen
(74) *Attorney, Agent, or Firm* — Oliff PLC

(57) ABSTRACT

The present invention relates to water-soluble modified lignins preparable by enzymatic reaction of at least one water-insoluble lignin with at least one organic compound which possesses at least one group selected from primary or secondary amino group, hydroxyl group and phenyl group and has an average molecular weight in the range from 75 to 2500 g/mol. The water-soluble modified lignins are preparable under mild conditions in a simple process. They can be used as dispersants for mineral binder compositions, where they act as plasticizers and in so doing prolong the setting time to much less of an extent than the water-insoluble lignins used in their preparation.

16 Claims, No Drawings

ENZYMATICALLY MODIFIED LIGNINS

TECHNICAL FIELD

The invention relates to enzymatically modified lignins, a process for preparing them and their use dispersants for mineral binders.

PRIOR ART

Lignin, after cellulose, is the most widespread natural polymer worldwide. It is obtained as a by-product in the production of pulp and is extensively burnt for energy and raw materials recovery. Only around 5% of the pulp plants operate using the sulphite process, in which lignosulphonate, also called ligninsulphonate, is obtained, being water-soluble and useful as a dispersant. Because around 95% of the pulp plants operate according to the kraft process, the majority by-product is the water-insoluble kraft lignin. In biorefineries as well, which convert wood and lignocellulose into bioethanol, lignin is a by-product. In the majority of cases, however, lignin is burnt for energy recovery. A more high-grade use for this renewable raw material is desirable, however, in order for lignin to be able to be utilized as a dispersant in aqueous media, it must be water-soluble or modified to make it so.

EP 0 367 389 describes the preparation of a dispersant by reaction of lignin with formaldehyde and subsequent sulphonation. This process uses toxic chemicals such as formaldehyde and sulphur dioxide, and high reaction temperatures.

EP 0 669 953 claims a process for preparing polymers which comprise lignin and organic compounds. There are no indications that the reaction products are water-soluble at a pH 7 or below or are suited to use as dispersants.

EP 1 040 145 describes the enzymatic grafting of ethylenically unsaturated monomers onto lignin using radically oxidizing enzymes in the presence of organic peroxides or hydroperoxides. There are no indications that the products obtained are soluble in water at a pH of 7 or below.

SUMMARY OF THE INVENTION

It is an object of the present invention to provide water-soluble modified lignins which are preparable in a simple process under mild conditions from water-insoluble lignins by reaction with organic compounds and can be used as dispersants for mineral binder compositions.

Surprisingly this object is achieved by a water-soluble modified lignin as described in Claim 1. It is preparable in a simple manner under mild conditions and without toxic chemicals, such as formaldehyde, for example, by enzymatic reaction from water-insoluble lignin and at least one organic compound. The water-soluble modified lignin is based largely on renewable raw materials, a desirable feature in many applications, and is easy to handle.

The reaction is catalysed by enzymes. It can therefore be accomplished under mild conditions, with no need for aldehydes, ketones or similar compounds in order to link the organic compound to the lignin, as is otherwise customary in the prior art in the chemical modification of lignin. This is an advantage, since the majority of aldehydes, especially formaldehyde, or ketones which are used for this purpose are substances objectionable on health grounds.

The water-soluble modified lignin of the invention is outstandingly suitable as a dispersant for mineral binders. In this application it exerts a significant activity as a plasticizer, with the highly desirable feature, consequently, of allowing the water content of a mineral binder composition to be lowered while retaining workability. Surprisingly, in addition to its activity as a plasticizer, it brings about a much smaller retardation of the setting of the mineral binder composition, as compared with the water-insoluble lignin used for the preparation process—again, a highly desirable feature. The cured mineral compositions produced using the lignin have the same good mechanical properties.

Further aspects of the invention are subjects of further independent claims.

Particularly preferred embodiments of the invention are subjects of the dependent claims.

CERTAIN EMBODIMENTS OF THE INVENTION

A subject of the invention is a water-soluble modified lignin ML, preparable by enzymatic reaction of at least one water-insoluble lignin L with at least one organic compound V which possesses at least one group selected from primary or secondary amino group, hydroxyl group and phenyl group and has an average molecular weight $M_n$ in the range from 75 to 2500 g/mol.

A lignin is said to be "water-soluble" when at least 95 weight % of 1.0 g of the dried lignin has dissolved in 100 g of deionized water at 20° C. after 30 minutes with stirring.

A lignin is said to be "water-insoluble" when less than 100 mg (10 weight %) of 1.0 g of the dried lignin has dissolved in 100 g of deionized water at 20° C. after 30 minutes with stirring.

Lignins which meet neither of these conditions are deemed "partially water-soluble".

By "molecular weight" in the present document is meant the molar mass (in grams per mole) of a molecule. The "average molecular weight" refers to the weight average $M_w$ or the number average $M_n$ of an oligomeric or polymeric mixture of molecules, and is determined as described in the Examples.

The water-soluble modified lignin ML consists of a fraction which originates from the water-insoluble lignin L and a fraction which originates from the organic compound V. The fraction which originates from the water-insoluble lignin L is preferably at least 20 weight %, more preferably at least 40 weight %, very preferably at least 50 weight %.

The water-soluble modified lignin ML preferably has an average molecular weight $M_w$ in the range from 1000 to 150 000 g/mol, preferably 1000 to 40 000 g/mol, more particularly 1000 to 20 000 g/mol.

Suitable water-insoluble lignin L for preparing the water-soluble lignin ML comprises all lignins, irrespective of origin and pretreatment. Particularly suitable are those known as kraft lignins, Organosolv lignins, soda lignins, acid lignins or lignins from the enzymatic degradation of cellulose in lignin-containing substances.

Kraft lignins are typically obtained in the production of pulp from wood by the kraft process, also called sulphate process. The kraft lignin can be isolated from the alkaline black liquor by various methods. Methods employed industrially for isolating lignin from the black liquor are, for example, the LignoBoost process or the LignoForce™ process.

Organosolv lignins are typically obtained in the Organosolv process, which can be used in pulp production or else in biorefineries. Here, the lignin is leached from wood or other lignin-containing materials at high temperatures by means of a water/solvent mixture. The lignin thus isolated is particularly pure. One example of such a lignin is Lignol HP™ from Lignol, Canada.

Soda lignins are typically obtained in the recovery of pulp by the soda process from annual plants such as grasses or straw, for example. One example thereof is Biosurfact 8000, produced by ALM in India.

Acid lignins come about during treatment of lignin-containing substances, for example wood, green horticultural waste, algae or grasses, with strong acids. In this operation, the substances broken down by the acids or soluble in acids are dissolved, and the acid-insoluble lignin can be separated off.

Other examples of the production of suitable lignins are the steam treatment of lignin-containing materials and subsequent enzymatic degradation of the cellulose.

The person skilled in the art is aware that different production processes and different lignin-containing raw materials may give rise to variation in the structure of the lignin, especially the molecular weight and the number of functional groups. Moreover, lignin may also contain impurities such as, for example, degradation products of cellulose, hemicelluloses or proteins, or salts.

One water-insoluble lignin L which is suitable for the invention comes, in particular, from a lignin-containing material of a kind occurring in nature, more particularly softwood, hardwood or straw. A lignin from wood or straw is preferred. Particularly preferred is a lignin from softwood or an Organosolv lignin from hardwood, more particularly a lignin from softwood.

Mixtures of different lignins may also be used.

In the enzymatic reaction with the organic compound V, the water-insoluble lignin L may be used as powder or in solution, for example as an Na salt in alkaline aqueous solution, or in solution in a mixture of water and acetone or water and dioxane in a volume ratio in the range from 50:50 to 80:20. Its use as a powder or as an Na salt in alkaline aqueous solution is preferred. In this way it is possible to operate without organic solvents. An advantage of its addition as a powder is that the step of dissolving the lignin is removed. An advantage of adding it as an Na salt is that the reaction mixture is particularly homogeneous.

The water-soluble lignin ML is prepared using an organic compound V which possesses at least one group selected from primary or secondary amino group, hydroxyl group and phenyl group and has an average molecular weight $M_n$ in the range from 75 to 2500 g/mol.

The organic compound V is preferably selected from the group consisting of

A) compounds of the formula (I),

$$Z_x-R-G-R-W_y \quad (I)$$

where
Z independently at each occurrence is —OH, —NH$_2$, O—R$^1$ or R$^1$,
G is a phenylene or naphthylene radical,
R independently at each occurrence is a covalent bond or a linear or branched, aliphatic hydrocarbon radical having 1 to 8 C atoms and optionally comprising unsaturated fractions, and more particularly is a covalent bond,
R$^1$ independently at each occurrence is an alkyl group having 1 to 4 C atoms,
x is 1 or 2 or 3,
y is 1 or 2 or 3, and
W is —COOM, —SO$_3$M, —OSO$_3$M, —PO$_3$M$_2$ or —OPO$_3$M$_2$, where M is H, an alkali metal, an alkaline earth metal, a di- or trivalent metal or an organic or inorganic ammonium;

B) compounds of the formula (II)

$$E + AO \rightarrow_n + BO \rightarrow_m R^2 \quad (II)$$

where
E is a phenoxy group or a primary amino group,
A and B independently of one another are an alkylene radical having 2 to 4 C atoms,
(n+m) is 1 to 50, and
R$^2$ is H, an alkyl group having 1 to 8 C atoms, —COOM, —SO$_3$M, —OSO$_3$M, —PO$_3$M$_2$ or —OPO$_3$M$_2$;

C) amino acids, more particularly one of the 21 natural alpha-aminocarboxylic acids;
and
D) aliphatic, linear or branched aminosulphonic acids having 2 to 10 C atoms.

Preferably n is 0 to 50. Preferably m is 0 to 50.

If the organic compound V possesses an acid group, said group may take the form of the free acid or a salt. In the case of a salt, the cation may be the ion of an alkali metal, of an alkaline earth metal, of a mono-, di- or trivalent metal, or an organic or inorganic ammonium. Preferred among these is sodium, potassium or calcium.

Preferred compounds of the formula (I) are aromatic compounds having at least one sulphonic acid group or carboxylic acid group and at least one amino group bonded to the phenylene or naphthylene radical, more particularly 4-amino-3-hydroxybenzoic acid, 3-amino-4-hydroxybenzoic acid, anthranilic acid, 4-aminosalicylic acid, 4-aminobenzoic acid, sulphanilic acid, 4-aminobenzene-1,3-disulphonic acid, 4-amino-5-hydroxy-2,7-naphthalenedisulphonic acid, 5-amino-2-methylbenzenesulphonic acid, 4-amino-3-methylbenzenesulphonic acid or 8-amino-3-methylbenzenesulphonic acid.

Preferred among these are compounds having a sulphonic acid group.

Further preferred among these is sulphanilic acid, 4-aminobenzoic acid or 5-amino-2-methylbenzenesulphonic acid.

Particularly preferred is sulphanilic acid or 4-aminobenzoic acid.

Preferred compounds of the formula (II) are compounds of the formula (II) in which E is a primary amino group, A is an ethylene radical, B is a 1,2-propylene radical, R$^2$ is a methyl group, and either n is 2 to 50 and m is 0 or n is 10 to 50 and m is 0 to 10. Especially suitable are Jeffamine® products from Huntsman, especially Jeffamine® M-2070.

Additionally preferred compounds of the formula (II) are compounds of the formula (II) in which R$^2$ is —OPO$_3$M$_2$. In this case these compounds, in addition to the monoester, may also contain fractions of diester and/or triester, as may likewise be obtained alongside the monoester in the preparation of phosphate esters by esterification of an alcohol with phosphoric acid, polyphosphoric acid or phosphoric acid pentoxide.

Preferred amino acids are alpha-aminocarboxylic acids, more particularly selected from the group consisting of glycine, alanine, glutamic acid, aspartic acid, tyrosine, serine, histidine and arginine.

Preferred aminosulphonic acids are linear aminosulphonic acids having 2 to 4 C atoms, more particularly taurine.

For preparing the water-soluble modified lignin ML, the water-insoluble lignin L may also be enzymatically reacted with a mixture of two or more organic compounds V. Such a mixture may comprise, for example, a compound of the formula (I) and a compound of the formula (II) or an amino acid or an aminosulphonic acid, or it may comprise more than one compound of the formula (I) or of the formula (II), or two or more amino acids or aminosulphonic acids.

The water-soluble lignin ML is prepared by enzymatic reaction. Enzymes are biocatalysts which are specialized in specific reactions. Not all enzymes, therefore, are suitable for the reaction described.

Suitability is possessed, for example, by peroxidases or, in particular, phenol oxidases, such as, in particular, laccases or tyrosinases.

In the enzymatic reaction there is preferably at least one enzyme selected from laccases or tyrosinases.

The enzyme used may be bacterial, vegetable or else fungal in origin.

Preference is given to laccases of fungal origin, especially the laccase from Trametes versicolor (available from Sigma Aldrich). Further preferred are laccases which retain their activity even under alkaline conditions.

Particularly suitable tyrosinases are fungal tyrosinases (available from Sigma Aldrich).

Particularly suitable peroxidases are radish peroxidases (available from Sigma Aldrich).

For the reaction, these enzymes need oxygen, in the case of the laccases and tyrosinases, the atmospheric oxygen present is typically sufficient. When using peroxidases it is advantageous if an oxygen source is additionally present for the reaction, such as a small amount of hydrogen peroxide, for example. The enzyme may be used in solution or as a powder, in purified or crude extract form, and/or immobilized on a carrier.

When the desired reaction conversion has been reached, the enzyme can be deactivated, in particular by heating of the reaction mixture to at least 80° C., preferably at least 90° C.

The activity of an enzyme is customarily expressed in U/mg (units per milligram) or U/ml (units per milliliter). The units indicate how many moles of a particular test substance are converted per minute under standard conditions. Since the activity of an enzyme is dependent on the test conditions such as pH, test substance and temperature, it may vary greatly. When reference is made in this patent application to U/mg or U/ml, the figures of the enzyme manufacturer have been used; they are not, therefore, the effective activities under the reaction conditions.

In the enzymatic reaction it is possible with preference to use a mediator. A mediator for enzymatic reactions is a substance which is activated by the enzyme and transfers the activation to the substrate—in this case, to the water-insoluble lignin L and/or to the organic compound V. As a result, the reaction can be accelerated. There are many mediators for laccases, and they are known to the person skilled in the art. One suitable mediator for laccases is, in particular, 2,2'-azinobis(3-ethylbenzothiazoline-6-sulphonic acid) (ABTS) or 2,6-dimethoxyphenol (DMP) or an extract of natural substances, particularly a tea extract or a wood extract, more particularly in the form of a hot-water extract of tea and/or of woodchips or sawdust. Preferred mediators for the reactions with laccase are extracts of black tea, green tea or wood, since they are inexpensive and non-toxic.

A preferred reaction medium for the enzymatic reaction for preparing the water-soluble modified lignin ML is water or a mixture of water and an organic solvent, more particularly acetone or dioxane. The fraction of the organic solvent in the reaction mixture is preferably less than 10 weight %, more particularly less than 5 weight %, and most preferably the reaction is operated entirely without organic solvents. Where the water-insoluble lignin L is used in solution in water/acetone or water/dioxane, the reaction medium contains small fractions of acetone or dioxane, respectively.

Preferably, therefore, the enzymatic reaction is carried out in a reaction medium comprising water and optionally at feast one organic solvent, the solvent fraction being preferably less than 10 weight %, more particularly less than 5 weight %, based on the total reaction mixture, and the reaction takes place most preferably entirely without organic solvents.

The pH of the reaction mixture in the enzymatic reaction may be adjusted by adding bases or acids. Preferred bases are ammonia, NaOH or KOH. Preferred acids are inorganic acids, such as especially hydrochloric acid, sulphuric acid, sulphurous acid, phosphoric acid or phosphorous acid, or organic acids, such as especially formic acid or acetic acid or alkylsulphonic acids. Also possible is the use of buffer solutions such as, in particular, Tris-HCl buffer or universal buffers such as, in particular, McIlvaine or Britton Robinson buffer. Where the organic compound V has an acid group and/or an amino group, it may be utilized wholly or partly for adjusting pH in the enzymatic reaction.

The enzymatic reaction is carried out preferably under mild conditions. More particularly it is carried out at a pH in the range from 2 to 11, preferably 5 to 10, more particularly 6 to 10. Since many laccases are no longer active at a pH above 8, reaction at a pH in the range from 6 to 8 is preferred for such laccases. For alkali-stable laccases, reaction at a pH in the range from 8 to 10 is preferred. For peroxidases and tyrosinases, the preferred pH is in the range from 6 to 9.

In the enzymatic reaction for preparing the water-soluble modified lignin ML, preferably 0.4 to 15 mmol, more preferably 0.8 to 10 mmol, more particularly 1 to 5 mmol, most preferably 1 to 3 mmol, of the organic compound V are used per gram of water-insoluble lignin L.

The suitable amount of enzyme for the enzymatic reaction varies according to enzyme type, reaction conditions, pH, and type and amount of organic compound V. The enzyme is used preferably in an amount such that the water-insoluble lignin L has undergone conversion to the water-soluble modified lignin ML in less than 3 days, preferably in less than 2 days, more particularly in less than 24 hours.

The suitable amount of water-insoluble lignin L in the reaction mixture is dependent on the reaction conditions and on the particular organic compound V. It is bounded at the top end by the consideration that the reaction mixture is still to be stirrable.

Where laccases or tyrosinases are used as enzymes, the enzymatic reaction is either stirred vigorously enough for atmospheric oxygen to be available for the reaction, or air may be passed temporarily or continuously through the solution, in the form of compressed air, for example. Where peroxidases are used as enzymes, hydrogen peroxide is preferably added to the solution in an amount such that the concentration of $H_2O_2$ in the solution remains below 1 mM, preferably below 0.1 mM.

A further subject of the invention is a process for preparing the water-soluble modified lignin ML, as described above, by enzymatically reacting a water-insoluble lignin L with at least one organic compound V, the organic compound V possessing at least one group selected from primary or secondary amino group, hydroxyl group and phenyl group and having an average molecular weight $M_n$ in the range from 75 to 2500 g/mol.

This process is carried out preferably in the manner already described.

From the process described, the water-soluble modified lignin ML is obtained as a constituent of a reaction product, the "reaction product" referring to the reaction mixture at the end of the enzymatic reaction, having been freed completely or partially from water and any solvents present, optionally by drying, more particularly spray drying, or evaporating.

A further subject of the invention is therefore the reaction product from the process described, comprising the water-soluble modified lignin ML, as described above.

In addition to the water-soluble modified lignin ML, the reaction product may comprise further constituents, such as, in particular, unconverted reactants, the enzymes or mediators used, and also salts or by-products.

The reaction product can be used without further work-up as a solution or in partially or fully dried form, in the same way as the water-soluble modified lignin ML, as described hereinafter.

The reaction product in dried form is water-soluble, meaning that it dissolves to an extent of at least 95 weight % when 50 mg are dissolved in 5 ml of deionized water at 20° C., after 30 minutes with stirring. It preferably dissolves in the same way even in a buffer solution at a pH of 7 or less, preferably at a pH of 6 or less, more preferably at a pH of 5 or less, most preferably at a pH of 4 or less.

A further subject of the invention is the use of the water-soluble modified lignin ML or of the reaction product comprising it as a dispersant for compositions comprising at least one mineral binder.

In the case of use as a dispersant, there is an improvement in particular in the workability of the composition comprising mineral binders. The mixing of the mineral binders with water is improved such that it takes place more uniformly and more easily. Furthermore, the water-soluble modified lignin ML, or the reaction product comprising it, acts as a plasticizer in the composition, with a particular advantage. As a result of the plasticizer activity, there is an increase in the flowability and processability of the mineral composition without any need to increase the water fraction, this being an advantage.

Alternatively, the water fraction in the composition on processing can be reduced without any detriment to the workability, this being a highly desirable quality.

Surprisingly, the water-soluble modified lignin ML or the reaction product comprising it retards the setting of the composition to much less of an extent than if the water-insoluble lignin L used for the preparation is employed as dispersant.

A suitable mineral binder is, in particular, a mineral binder which reacts in the presence of water to form solid hydrates or hydrate phases, in a hydration reaction. More particularly it is a hydraulic binder which can be hardened with water even under water, such as, in particular, cement or hydraulic lime, or a latent hydraulic binder which sets with water under the action of adjuvants, such as, in particular, slag, or pozzolanic binders such as, in particular, flyash, or a non-hydraulic binder such as, in particular, gypsum in the form of anhydrite or hemihydrate gypsum.

The mineral binder is preferably selected from the group consisting of cement, gypsum, burnt lime and flyash.

Particularly preferred as mineral binder is cement, more particularly a cement according to European Standard EN 197-1 or a sulphoaluminate cement or an aluminous cement.

Most preferred is a cement containing Portland cement according to EN 197-1. A further subject of the invention is a composition comprising
  at least one mineral binder,
  at least one water-soluble modified lignin ML, as described above, and,
  optionally water.

A composition of this kind combines a relatively low water content with very good workability, more particularly a high flowability and a rapid setting time.

The mineral binder is, in particular, a mineral binder which reacts in the presence of water to form solid hydrates or hydrate phases, in a hydration reaction. More particularly it is a hydraulic binder which can be hardened with water even under water, such as, in particular, cement or hydraulic lime, or a latent hydraulic binder which sets with water under the action of adjuvants—in particular, slag, or pozzolanic binders such as, in particular, flyash, or a non-hydraulic binder such as, in particular, gypsum in the form of anhydrite or hemihydrate gypsum.

The mineral binder is preferably selected from the group consisting of cement, gypsum, burnt lime and flyash.

Particularly preferred as mineral binder is cement, more particularly a cement according to European Standard EN 197-1 or a sulphoaluminate cement or an aluminous cement.

Most preferred is a cement containing Portland cement according to EN 197-1.

The water-soluble modified lignin ML is used preferably in an amount of 0.05 to 5 weight %, more preferably 0.1 to 2 weight %, more particularly 0.15 to 2 weight %, based on 100 weight % of mineral binder.

The water-soluble modified lignin ML is present in particular in the form of a reaction product, as described above.

The composition may additionally comprise further substances, such as, in particular, the following:
  admixtures of the kind customarily used in mineral binder compositions, such as, in particular, silica fume, slag sands, flyash or limestone fillers;
  aggregates, such as, in particular, sand, gravel, stones, finely ground quartz, or chalks;
  concrete plasticizers, such as, in particular, lignosulphonates, sulphonated naphthalene-formaldehyde condensates, sulphonated melamine-formaldehyde condensates, polysaccharides, or derivatives thereof; or polycarboxylate ethers;
  or further auxiliaries, such as, in particular, accelerators, corrosion inhibitors, retarders, shrinkage reducers, defoamers or air entrainers.

The composition is produced preferably by providing at least one mineral binder and at least one water-soluble modified lignin ML and then mixing them with one another.

Other substances in the composition may have been mixed with the mineral binder beforehand and possibly stored, or they may have been mixed with the water-soluble modified lignin ML beforehand and stored, or they may be added shortly before, during or shortly after the mixing of the mineral binder and the water-soluble modified lignin ML and mixed into the composition.

The setting of the composition begins through the addition of wafer. The mineral binder forms a solid structure in this process.

The amount of water is preferably selected such that the composition has a desired working consistency. More particularly the composition has a high flowability, allowing it to be pumped or otherwise conveyed, and such that it flows well when spread. With further preference, the minimum possible amount of water is used, so that not too much excess water remains in the cured composition after setting, since excess water reduces the strength qualities. The appropriate amount of water is heavily dependent on the nature and fineness of the mineral binder, the nature, amount and fineness of the aggregates, the amount of the water-soluble modified lignin ML, and any other substances present.

The amount of water added to such a composition is also referred to as tempering water. In the case of cement as mineral binder, it is expressed using w/c. The w/c indicates the amount of water in grams relative to the amount of cement in grams.

A further subject of the invention is a shaped body obtained by setting and curing the above-described composition after contact thereof with water. This shaped body has a three-dimensional form.

The shaped body preferably constitutes a component of a building, such as, in particular, a structural shell, a wall, a floor, a coating, a screed or a filling.

A further subject of the invention is a dispersant for mineral binders, comprising at least one water-soluble modified lignin ML, as described above.

The dispersant may be present in solid form, as a powder or granules, for example.

The dispersant preferably comprises water. It may be present in particular as a solution, suspension or paste.

The dispersant may comprise further customary additives. These may in particular be other plasticizers, examples being other modified lignins, lignosulphonates, sulphonated naphthalene-formaldehyde condensates, sulphonated melamine-formaldehyde condensates, polysaccharides or derivatives thereof, or polycarboxylate ethers (PCE). Further possible additions are stabilizers, antioxidants, dyes, accelerators, retarders, shrinkage reducers, defoamers, air entrainers or foam formers.

The dispersant preferably has a water-soluble modified lignin ML content in the range from 5 to 100 weight %, more particularly 10 to 90 weight %.

The water-soluble modified lignin ML and/or the dispersant may be used in particular, in a composition comprising at least one mineral binder, as plasticizer, for improving the workability and/or for improving the flowability, or as wafer reducers, in other words for reducing the amount of water for a given set of processing properties.

The water-soluble modified lignin ML and/or the dispersant may be used in the solid aggregate state, in the form of powder or granules, for example. Solid additions of this kind are easy to transport and store.

In the solid aggregate state, the water-soluble modified lignin ML may be a constituent of a so-called dry mix, of a cement composition, for example. A dry mix of this kind is typically packed in sacks or is stored in silos, if can be used even after relatively long-term storage, and has good pourability.

The water-soluble modified lignin ML and/or the dispersant may be added to a composition comprising at least one mineral binder shortly before or shortly after or together with the addition of the tempering wafer. In one preferred embodiment the addition is made in the form of an aqueous solution or dispersion, more particularly as tempering wafer or as part of the tempering water. The aqueous solution is produced in particular by subsequent combining with water.

The water-soluble modified lignin ML may be added to a composition comprising at least one mineral binder, or alternatively, before or during the operation of grinding the composition, such as the operation of grinding cement clinker to form cement.

When the water-soluble modified lignin ML is used as a dispersant for mineral binders, an advantageous plasticizing effect is achieved, without an undesirably high increase in the setting time.

EXAMPLES

Set out hereinafter are working examples which are intended to illustrate the invention described. The invention is of course not confined to these working examples described.

"Ref." stands for "Reference Example"

Description of the Measurement Methods

The average molecular weight of the water-insoluble lignins and of the water-soluble modified lignins was determined by SEC analysis. The SEC analysis was carried out on an HPLC system equipped with a column cascade from Polymer Standards Service GmbH (MCX 10 μm 1000 Å, MCX 10 μm 100 000 Å+pre-column) and a UV detector at 254 nm. The eluent and solvent used for the samples was 0.01 N aqueous sodium hydroxide solution. Measurement took place at 40° C. with an eluent flow rate of 0.5 ml/min. Calibration took place using 5 narrow polymer standards of sulphonated polystyrene in the molecular weight range $M_w$ from 1800 to 400 000 g/mol and p-toluenesulphonic acid.

The amount of organic compound V in the reaction mixture was determined by HPLC. The difference between the amount of organic compound at the start of the reaction and the amount of organic compound after a defined reaction time was used to calculate the "reaction conversion in %".

Measuring conditions for the HPLC analysis:
Eluent A: 1.5 g of formic acid in 1 l of deionized water
Eluent B: acetonitrile
Eluent flow rate 1.5 ml/min
Linear gradient from 100% A to 80% A over 20 minutes
Column: Inertsil® ODS-3, 150 mm, 5 μm (GL-Sciences, Japan)

The chromatograms were evaluated by UV at the wavelengths characteristic of the compounds in question: at 248 nm for sulphanilic acid, at 290 nm for 4-aminobenzoic acid, and at 263 nm for 5-amino-2-methylbenzenesulphonic acid.

Water-Insoluble Lignins L Used

The average molecular weight of the lignins was determined by the method described in the examples.

Lignin-1: Kraft lignin from softwood (Indulin® AT from MeadWestvaco, USA) with $M_w$ of 6000 and $M_n$ of 2000

Lignin-2: Organosolv lignin from spruce (softwood; pilot plant, Germany) with $M_w$ of 6000 and $M_n$ of 2100

Lignin-3: Organosolv lignin from beech (hardwood; pilot plant, Germany) with $M_w$ of 15 400 and $M_n$ of 2400

Lignin-4: Grass lignin (Biosurfact 8000 from ALM, India) with $M_w$ of 4100 and $M_n$ of 1500

Lignin-5: Organosolv lignin from hardwood (Lignol HP-L™ from Lignol, Canada) with $M_w$ of 8800 and $M_n$ of 2200.

The moisture content of the water-insoluble lignins used was determined using a halogen dryer from Mettler Toledo and taken into account in the amount of the lignins used.

"Lignin_Na salt solution" refers to an aqueous solution prepared by suspending a quantity of lignin containing 10 g of dry lignin in about 50 ml of deionized water, then adding sufficient 1N sodium hydroxide solution to dissolve 98 to 100 weight % of the lignin, and making up the solution to 100 ml with deionized water. A lignin_Na salt solution prepared accordingly contains 100 mg of lignin per milliliter.

"Lignin_Na salt" refers to the solid obtained after drying of the lignin_Na salt solution at 70° C. in an oven to constant weight.

Enzymes Used:

Laccase Solution:

From laccase (laccase from Trametes versicolor from Sigma Aldrich, Switzerland) a solution having an activity of 12 U/ml was prepared with deionized water.

Tyrosinase Solution:

From fungal tyrosinase (from Sigma Aldrich, Switzerland) a first solution with 250 U/ml and a further solution with 5000 U/ml were prepared using deionized water.

Additional Substances Used and Abbreviations:

Abts Solution:

Aqueous solution of the mediator ABTS (2,2'-azinobis(3-ethylbenzothiazoline-6-sulphonic acid) in a concentration of 1 mmol per liter.

Buffer solution pH 7: Aqueous buffer solution containing 17.65 ml of 0.1 M citric acid monohydrate solution and 82.35 ml of 0.2 M disodium hydrogenphosphate solution in 100 ml.

Buffer solution pH 4: Buffer solution pH 4 from Metrohm, Switzerland.

Preparation of Reaction Products Containing Water-Soluble Modified Lignin ML

Example 1

In a 100 ml round-bottomed flask, 73 ml of deionized water, 5 ml of an aqueous solution of sulphanilic acid Na salt (100 mM), 10 ml of ABTS solution and 2 ml of lignin-1_Na salt solution were mixed with one another and the pH was adjusted with 1N HCl to about 7. Then 10 ml of laccase solution were added. A reflux condenser was mounted on the round-bottomed flask. The reaction mixture was stirred vigorously for 94 hours at 30-35° C. with a magnetic stirrer and from time to time a determination was made of the reaction conversion, as reported in Table 1. Thereafter the reaction mixture, without further purification, was concentrated on a rotary evaporator. This gave a brown-black solid having an average molecular weight $M_w$ of 17 900 g/mol and $M_n$ of 4600 g/mol for the water-soluble modified lignin ML contained therein.

Example 2

Example 1 was repeated but using an aqueous solution of 4-aminobenzoic acid Na salt (100 mM) instead of the solution of sulphanilic acid Na salt. This gave a brown-black solid having an average molecular weight $M_w$ of 16 600 g/mol and $M_n$ of 3900 g/mol for the water-soluble modified lignin ML contained therein.

TABLE 1

Conversion of sulphanilic acid or 4-aminobenzoic acid after the specified reaction times

|  | Example 1 | Example 2 |
| --- | --- | --- |
| Conversion after 22 hours | 7% | 5% |
| Conversion after 46 hours | 10% | 15% |
| Conversion after 70 hours | 27% | 41% |
| Conversion after 94 hours | 29% | 43% |

Comparative Reactions without Lignin

Example 1 and Example 2 were repeated, but using the buffer solution pH 7 instead of deionized water, and water instead of the lignin-1_Na salt solution. After a reaction time of 70 hours, the conversion of sulphanilic acid Na salt and 4-aminobenzoic acid Na salt, respectively, was found to be 0%. There had therefore been no reaction of the sulphanilic acid or of the 4-aminobenzoic acid with the laccase.

Comparative Reactions without Laccase

Example 1 and Example 2 were repeated, but using deionized water instead of the laccase solution. After a reaction time of 70 hours, the conversion of sulphanilic acid and 4-aminobenzoic acid, respectively, was found to be 0%. There had therefore been no reaction of the sulphanilic acid or of the 4-aminobenzoic acid with the lignin.

Examples 3 to 6

Examples 3 to 6 were carried out like Example 1, but using the reagents of Table 2 in the specified amounts. The reaction mixture was freeze-dried at the end of the reaction in each case. In each case a water-soluble, brown-black powder was obtained.

TABLE 2

Reagents used in the specified amounts and conversion of sulphanilic acid or 4-aminobenzoic acid after 24 h

|  | Example 3 | Example 4 | Example 5 | Example 6 |
| --- | --- | --- | --- | --- |
| Deionized water | 29.2 ml | 29.2 ml | 27.2 ml | 29.2 ml |
| ABTS solution (1 mM) | 4.0 ml | 4.0 ml | 4.0 ml | 4.0 ml |
| Sulphanilic acid Na salt solution (100 mM) | 2.0 ml | — | 2.0 ml | 1.0 ml |
| 4-Aminobenzoic acid Na salt solution (100 mM) | — | 2.0 ml | 2.0 ml | 1.0 ml |
| Lignin-1_Na salt solution (100 mg/ml) | 0.8 ml | 0.8 ml | 0.8 ml | 0.8 ml |
| HCl 1N | 0.13 ml | 0.13 ml | 0.13 ml | 0.13 ml |
| Laccase solution (12 U/ml) | 4.0 ml | 4.0 ml | 4.0 ml | 4.0 ml |
| pH of reaction mixture | 5.9 | 6.0 | 6.0 | 6.0 |
| Conversion of sulphanilic acid/4-aminobenzoic acid after 24 hours | 30% | 43% | 18%/40% | 14%/44% |

Example 7

In a 250 ml round-bottomed flask, 68.2 ml of deionized water, 4.0 ml of an aqueous solution of sulphanilic acid Na salt (100 mM) and 1.6 ml of lignin-1_Na salt solution were mixed with one another and the pH was adjusted with 1N HCl to about 6. Then 8.0 ml of laccase solution were added. The reaction flask was closed with an open ground-glass tap, fitted with a balloon filled with compressed air. The reaction mixture was stirred vigorously at 30-35° C. for 4 days, using a magnetic stirrer. Within this time, the compressed-air balloon was refilled a number of times. The conversion of sulphanilic acid after 4 days was 20%. The reaction mixture, without further work-up, was dried in an oven at 70° C. This gave a brown-black solid having an average molecular weight $M_w$ of 20 000 g/mol and $M_n$ of 8000 g/mol for the water-soluble modified lignin ML contained therein. 50 mg of this product dissolved fully in 5 ml of buffer solution pH 4.

As a comparison, Example 7 was repeated, but adding deionized water instead of the sulphanilic acid Na salt solution—50 mg of the brown-black solid obtained in this case were not soluble in 5 ml of buffer solution pH 4.

As a further comparison, the lignin-1_Na salt solution was dried in an oven at 70° C. 50 mg of the brown-black solid obtained in this process were not soluble in 5 ml of buffer solution pH 4.

In a 250 ml round-bottomed flask, 30 ml of lignin-1_Na salt solution, 4 ml of ABTS solution and 30.0 ml of deionized water were mixed. With stirring, 0.70 g of sulphanilic acid was added. The pH was adjusted with 1N HCl to about 6. Then 8.0 ml of laccase solution and 8.0 ml of water were added. The reaction flask was closed with an open ground-glass tap, fitted with a balloon filled with compressed air. The reaction mixture was stirred vigorously at 30-35° C. for 72 hours, using a magnetic stirrer. During the reaction, the compressed-air balloon was refilled a number of times. The reaction mixture was heated at 95° C. for about 10 minutes and dried without purification in an oven at 70° C. This gave a brown-black solid having an average molecular weight $M_w$ of 14 600 g/mol and $M_n$ of 3000 g/mol for the water-soluble modified lignin ML contained therein, 50 mg of the resulting solid were completely soluble in 5 ml of buffer solution pH 4.

Examples 9 to 13

For each example, 20 ml of an aqueous sulphanilic acid Na salt solution (200 mM), 4 ml of ABTS solution and 30 mi of lignin_Na salt solution of the lignins specified in Table 3 (starting lignin) were mixed in a glass beaker. The pH was adjusted with 0.5 N HCl to 5.8. Then 6 ml of laccase solution were mixed in and the mixture was made up to 80 ml with deionized water. The reaction mixture was then transferred to a 250 ml round-bottomed flask and closed with an open ground-glass tap, fitted with a balloon filled with compressed air. The reaction mixture was stirred vigorously at 30-35° C. with a magnetic stirrer for 72 hours. During the reactions, the compressed-air balloon was refilled a number of times. The reaction mixtures, which at the end of the reaction time were not clear, were centrifuged in 50 ml centrifuge tubes at 8000 rpm. The supernatant solution and the insoluble fraction were separated and dried separately in an oven at 70° C. The soluble fraction of the reaction product, the reaction conversion, and the molecular weights of the resulting water-soluble, modified lignin ML are reported in Table 3.

TABLE 3

| | Starting lignin | Soluble fraction of reaction product | Reaction conversion | Modified lignin ML obtained | |
|---|---|---|---|---|---|
| | | | | $M_w$ (g/mol) | $M_n$ (g/mol) |
| Example 9 | Lignin-1 | 100% | 30% | 28300 | 4500 |
| Example 10 | Lignin-2 | 100% | 36% | 7200 | 2500 |
| Example 11 | Lignin-3 | 54% | 56% | not determined | not determined |
| Example 12 | Lignin-4 | 80% | 47% | 10500 | 2200 |
| Example 13 | Lignin-5 | 100% | 43% | 4600 | 1900 |

In a glass beaker, 40 ml of lignin-1_Na salt solution, 50 ml of an aqueous solution of sulphanilic acid Na salt (200 mM) and 20 ml of ABTS solution were mixed with one another and the pH was adjusted using 0.5 N HCl to 5.9. Then 30 ml of laccase solution were added and the mixture was made up with deionized water to 160 ml. The reaction mixture was transferred to a 500 ml single-necked flask, which was closed with an open ground-glass tap, fitted with a balloon filled with compressed air. The reaction mixture was stirred vigorously with a magnetic stirrer for 70 hours at 30-35° C., and during the reaction the compressed-air balloon was refilled a number of times. After 70 hours, 50% of the sulphanilic acid was converted. The resulting clear, dark brown solution was dried in a drying cabinet at 70° C. This gave a brown-black solid having an average molecular weight $M_w$ of 37 000 g/mol and $M_n$ of 4600 g/mol for the water-soluble, modified lignin ML contained therein. 50 mg of the resulting solid were completely soluble in 5 ml of buffer solution pH 4.

Example 15

Example 14 was repeated, but using a 4-aminobenzoic acid Na salt solution (200 mM) instead of the sulphanilic acid Na salt solution. After 70 hours, 45% of the 4-aminobenzoic acid had reacted. The clear, dark brown solution obtained was dried in a drying cabinet at 70° C. This gave a brown-black solid having an average molecular weight $M_w$ of 32 000 g/mol and $M_n$ of 4200 g/mol for the water-soluble, modified lignin ML contained therein. 50 mg of the solid obtained were partially soluble in 5 ml of buffer solution pH 4 and completely soluble in water at a pH of 8.

Example 16

Example 14 was repeated, but using 20 ml of deionized water instead of 20 ml of ABTS solution, and 70 mg of laccase (12 U/mg) in powder form and 30 ml of deionized water instead of 30 ml of laccase solution. After 24 hours, 25% and, after 48 hours, 39% of the sulphanilic acid had reacted. The resulting clear, dark brown solution was dried in a drying cabinet at 70° C. This gave a brown-black solid having an average molecular weight $M_w$ of 114 000 g/mol and $M_n$ of 7900 g/mol for the water-soluble, modified lignin ML contained therein. 50 mg of the resulting solid were completely soluble in 5 ml of buffer solution pH 4.

Examples 17 to 20

For each example, in a glass beaker, 2 ml of an aqueous solution of sulphanilic acid Na salt (100 mM), 30 ml of deionized water and 0.8 ml of the respective lignin-1 solution (100 mg/ml) or 80 mg of lignin-1 powder, in accordance with Table 4, were mixed. The pH was adjusted using 1N HCl or 0.1 N NaOH to 6.0. Then 4 ml of laccase solution were added and the mixture was made up to 40 ml with deionized water. The reaction mixture was transferred to a 100 ml round-bottomed flask, which was closed with an open ground-glass tap fitted with a balloon filled with compressed air. The reaction mixture was stirred vigorously at 30-35° C. with a magnetic stirrer for several hours, as reported in Table 4. During the reaction, the compressed-air balloon was refilled a number of times, and from time to time the reaction conversion was determined, as reported in Table 4.

TABLE 4

Nature of addition of lignin-1 and reaction conversion after defined reaction times

| | Example 17 | Example 18 | Example 19 | Example 20 |
|---|---|---|---|---|
| Lignin-1 in solution in | NaOH* | acetone/ $H_2O$** | dioxane/ $H_2O$** | as powder |
| Conversion after 21 hours | 19% | 16% | 14% | 7% |
| Conversion after 45 hours | 23% | 20% | 19% | 12% |
| Conversion after 70 hours | 28% | 21% | 21% | 16% |

*corresponds to lignin-1_Na salt solution
**volume ratio of solvent to water of 4:1

In a glass beaker, 8.0 ml of lignin-1_Na salt solution, 24 ml of deionized water and 0.25 g of taurine were mixed. The pH was adjusted using 1N NaOH to 9.0. Then 1.0 ml of tyrosinase solution (5000 U/ml) was added and the mixture was made up to 40 ml with deionized water. The reaction mixture was transferred to a 250 ml round-bottomed flask, which was closed with an open ground-glass tap, fitted with a balloon filled with compressed air. The reaction mixture was stirred vigorously at 20-25° C. with a magnetic stirrer for 47 hours. The compressed-air balloon was refilled a number of times during the reaction. The reaction mixture was dried in a drying cabinet at 70° C. This gave a brown-black solid having an average molecular weight $M_w$ of 11 000 g/mol and $M_n$ of 3100 g/mol for the water-soluble, modified lignin ML contained therein. 50 mg of the resulting solid were partially soluble in 5 ml of buffer solution pH 4 and completely soluble in 5 ml of buffer solution pH 7.

Example 22

In a conical centrifuge tube with a capacity of 40 ml, 0.8 ml of lignin-1_Na salt solution and 5 ml of an aqueous solution of histidine (20 mM) were mixed and the pH was adjusted using 1N HCl to 9. Then 2 ml of tyrosinase solution (250 U/ml) were added and the mixture was made up to 20 ml with deionized water. The closed centrifuge tube was shaken at 25° C. and 250 rpm for 48 hours. The resulting dark brown reaction mixture was freeze-dried to give a brown-black solid, 50 mg of this solid were completely soluble in buffer solution pH 7.

Example 23

In a 1 liter chicane flask, 20 ml of an aqueous solution of 5-amino-2-methylbenzenesulphonic acid Na salt (200 mM), 4 ml of ABTS solution and 30 ml of lignin-1_Na salt solution were mixed and the pH was adjusted using 1N HCl to 8. Then 6 ml of laccase solution were added and the mixture was made up with deionized water to 100 ml. The reaction mixture was shaken at 30° C. and 200 rpm for 8 days and from time to time the reaction conversion was determined, as reported in Table 5. The reaction mixture, without further purification, was freeze-dried to give a black-brown solid. 50 mg of this solid were completely soluble in 5 ml of buffer solution pH 4.

TABLE 5

Conversion of 5-amino-2-methylbenzenesulphonic acid after certain reaction times

| | Example 23 |
|---|---|
| Conversion after 24 hours | 59% |
| Conversion after 48 hours | 81% |
| Conversion after 72 hours | 86% |
| Conversion after 144 hours | 95% |

Use of the Water-Soluble Modified Lignin ML as Dispersant

Determination of the Yield Point:

In a plastic beaker, 25 g of cement were mixed thoroughly for 20 seconds, by hand using a spatula, with 9.5 g of water for a w/c of 0.38 or with 9.0 g of water for a w/c of 0.38, to give a cement paste. Where the cement paste was to contain a dispersant, this dispersant had been dissolved beforehand in an amount of 0.3 weight % to 100% of cement in the 9.5 g or 9.0 g of water. The cement paste was then introduced into a metal cylinder 22 mm in diameter and 50 mm in height, which was fastened into the mount of the rheometer (Physica MCR 301, Anton Paar, Austria; Rheoplus software). A metal helix with a height of 32 mm and a diameter of 20 mm was lowered into the cement paste. The cement paste was subjected to shearing by rotation of the helix, in accordance with a specified shearing profile, as described in Table 6, and the shearing stress was recorded as a function of the shear rate. After about 5 minutes and after about 30 minutes, at a shear rate of zero, the associated shearing stress in pascals (Pa) was read off from the plot of the decreasing shear rate, and represents the yield point of the cement paste. The lower the yield point, the better the flow of the cement paste.

TABLE 6

Shearing profile for determining the yield point

| Phase | Number of data points | Duration per data point (s) | Shear rate ($s^{-1}$) | |
|---|---|---|---|---|
| 1 | 30 | 1 | 100 | Mixing |
| 2 | 90 | 1 | 500 | Preliminary shearing |
| 3 | 30 | 10 . . . 1 log | 0.1-500 log | Increase in shear rate |
| 4 | 30 | 1 . . . 10 log | 500-0.1 log | Decrease in shear rate for determining the yield point after about 5 minutes |
| 5 | 100 | 1 | 0.1 | |
| 6 | 20 | 60 | 1 | Mixing slowly |
| 7 | 10 | 1 | 500 | Mixing up rapidly |
| 8 | 30 | 10 . . . 1 log | 0.1-500 log | Increase in shear rate |
| 9 | 30 | 1 . . . 10 log | 500-0.1 log | Decrease in shear rate for determining the yield point after about 30 minutes |
| 10 | 10 | 1 | 500 | Mixing up rapidly |

Determination of the Setting Time:

For determination of the setting time, after the determination of the yield point, about 10 g of the cement paste from the metal cylinder of the rheometer were introduced into a glass vessel, which was closed, and then monitored to ascertain the change over time in the heat of hydration of the cement paste, using isothermal microcalorimetry (TAM AIR, TA Instruments, USA). The setting time here represents the time elapsing between the mixing of the cement with water and the attainment of the maximum hydration temperature (after the induction phase or resting phase).

Examples 24 to 29

Determination of the yield point and of the setting time with cement CEM I 42.5, Normo 4 (from Holcim, Switzerland) at a w/c of 0.38 with the dispersants of Table 7.

TABLE 7

Yield point and setting time of cement pastes

| | Dispersant used | Yield point after about 5 minutes (Pa) | Yield point after about 30 minutes (Pa) | Setting time (hours) |
|---|---|---|---|---|
| Ref. 1 | None | 126 | 158 | 8.3 |
| Example 24 | Solid from Example 1 | 29 | 42 | 11.0 |
| Example 25 | Solid from Example 2 | 29 | 35 | 12.6 |
| Ref. 2 | Lignin-1_Na salt | 29 | 31 | 17.8 |
| Ref. 3 | None | 196 | 242 | not determined |
| Example 26 | Solid from Example 3 | 54 | 81 | not determined |
| Example 27 | Solid from Example 4 | 95 | 124 | not determined |
| Example 28 | Solid from Example 5 | 97 | 56 | not determined |
| Example 29 | Solid from Example 6 | 55 | 92 | not determined |

When used as dispersants, the water-soluble modified lignins of the invention exhibit a sharp reduction in the yield point and hence a good plasticizing effect in conjunction with a much shorter setting time than the water-insoluble lignin-1 used in their preparation.

When assessing the results in Table 7 it is important to bear in mind that the same cement was used in each case only for one measurement series (Ref. 1 and Example 24 and 25 and Ref. 2; and Ref, 3 and Examples 28 to 29), and so when comparing results from different measurement series, if is necessary to take account of slight fluctuations caused by the cement from different batches. This explains the discrepancies in values between Ref. 1 and Ref. 3.

Examples 30 and 31

Determination of the yield point of cement pastes produced with cement CEM I 42.5 (from three Swiss cement works, 1:1:1 in parts by weight) at a w/c of 0.36 with the dispersants as per Table 8. For comparison, an Na lignosulphonate (Avebene N9 from Avebene, France) was used as dispersant.

TABLE 8

Yield point of cement pastes

| | Dispersant used | Yield point after about 5 minutes (Pa) | Yield point after about 30 minutes (Pa) |
|---|---|---|---|
| Ref. 4 | None | 147 | 169 |
| Example 30 | Solid from Example 16 | 84 | 82 |
| Example 31 | Solid from Example 21 | 41 | 54 |
| Ref. 5 | Na lignosulphonate | 59 | 64 |

Production of Compositions (Mortar Mixtures)

Examples 32 to 39

In a mechanical mixer from Hobart. 750 g of cement CEM I 42.5 (from three Swiss cement works, 1:1:1 in parts by weight), 141 g of limestone filler (Nekafill 15 from Kalkfabrik Netsfal, Switzerland), 738 g of sand 0-1 mm, 1107 g of sand 1-4 mm and 1154 g of sand 4-8 mm were mixed dry for 1 minute. Over the course of 30 seconds, a mixture of 352.5 g of water for w/c 0.50 (Examples 38 and 39) or 382.5 g of water for w/c 0.54 (Examples 32 to 37) and 22.5 g of a 10 weight % strength aqueous solution of the solid from the respective example, defoamed with a commercial defoamer, as reported in Tables 9 and 10, was added, and mixing continued for 2.5 minutes. The total wet mixing time lasted 3 minutes in each case. In the same way, reference mortars were produced, but using 22.5 g of a likewise defoamed 10 weight % strength solution of the lignin-1_Na salt or of the Na lignosulphonate (Avebene N9 from Avebene, France). In the same way, additionally, mortar mixtures without dispersants were produced as comparatives, with 375 g of water for w/c 0.50 or with 405 g of water for w/c 0.54.

The compositions were tested as follows:
The flow value was determined according to EN 1015-3.
The air content was measured according to EN 1015-7.
The hydration behaviour was determined by measuring the temperature in the course of the time after mixing with water. The temperature measurement took place under adiabatic conditions, using a thermocouple as temperature sensor.

The setting time for these examples refers to the time elapsing between mixing with water and the attainment of the temperature maximum occurring after the induction phase or resting phase.

For the determination of the compressive strength of the cured mortars, mortar prisms of 4×4×16 cm were produced and, after demoulding, were stored at 20° C. and 95% relative humidity. The compressive strength after 24 hours and 7 days was determined according to EN 196-1.

TABLE 9

Properties of mortar mixtures

| | Dispersant | w/c | Air content (%) | Flow value (in mm) | | |
|---|---|---|---|---|---|---|
| | | | | 0 min | 30 min | 60 min |
| Ref. 6 | None | 0.54 | 2.5 | 162 | 152 | 149 |
| Example 32 | Solid from Example 9 | 0.54 | 2.3 | 176 | 142 | 144 |

TABLE 9-continued

Properties of mortar mixtures

| | Dispersant | w/c | Air content (%) | Flow value (in mm) 0 min | 30 min | 60 min |
|---|---|---|---|---|---|---|
| Example 33 | Solid from Example 10 | 0.54 | 2.4 | 190 | 162 | 148 |
| Example 34 | Water-soluble part of the solid from Example 11 | 0.54 | 2.3 | 182 | 152 | 144 |
| Example 35 | Water-soluble part of the solid from Example 12 | 0.54 | 2.3 | 162 | 150 | 142 |
| Example 36 | Solid from Example 13 | 0.54 | 2.4 | 182 | 148 | 138 |
| Example 37 | Solid from Example 23 | 0.54 | 2.0 | 196 | 175 | 170 |
| Ref. 7 | Na lignosulphonate | 0.54 | 2.4 | 176 | 146 | 138 |
| Ref. 8 | Lignin-1_Na salt | 0.54 | 2.3 | 174 | 160 | 152 |

TABLE 10

Properties of mortar mixtures and shaped bodies

| | Dispersant | w/c | Air content (%) | Flow value (in mm) 0 min | 30 min | 60 min | Setting time (h) | Compressive strength (Pa) 1 day | 7 days |
|---|---|---|---|---|---|---|---|---|---|
| Ref. 9 | None | 0.50 | 1.4 | 148 | 142 | 140 | 12.8 | 20.7 | 47.2 |
| Example 38 | Solid from Example 14 | 0.50 | 2.0 | 178 | 156 | 151 | 14.0 | 18.6 | 50.1 |
| Example 39 | Solid from Example 15 | 0.50 | 2.1 | 166 | 160 | 147 | 14.2 | 18.6 | 50.2 |
| Ref. 10 | Na lignosulphonate | 0.50 | 2.3 | 175 | 166 | 148 | 14.7 | 17.8 | 46.9 |
| Ref. 11 | Lignin-1_Na salt | 0.50 | 2.4 | 176 | 162 | 156 | 15.7 | 17.5 | 47.6 |

The invention claimed is:

1. A water-soluble modified lignin ML, prepared by enzymatic reaction of at least one water-insoluble lignin L with at least one organic compound V, the at least one organic compound V possessing at least one selected from the group consisting of a primary amino group, a secondary amino group, a hydroxyl group and a phenyl group, and has an average molecular weight $M_n$ in the range from 75 to 2500 g/mol,
wherein in the enzymatic reaction, at least one enzyme selected from the group consisting of peroxidases and phenol oxidases is present.

2. The water-soluble modified lignin ML according to claim 1, wherein the organic compound V is selected from the group consisting of A) compounds of the formula (I), $$Z_x\text{---}R\text{-}G\text{-}R\text{---}W_y \qquad (I)$$

where
Z independently at each occurrence is —OH, —NH$_2$, O—R$^1$ or R$^1$,
G is a phenylene or naphthylene radical,
R independently at each occurrence is a covalent bond or a linear or branched, aliphatic hydrocarbon radical having 1 to 8 C atoms and optionally comprising unsaturated fractions,
R$^1$ independently at each occurrence is an alkyl group having 1 to 4 C atoms, x is 1 or 2 or 3,
y is 1 or 2 or 3, and
W is —COOM, —SO$_3$M, —OSO$_3$M, —PO$_3$M$_2$ or —OPO$_3$M$_2$, where M is H, an alkali metal, an alkaline earth metal, a di- or trivalent metal or an organic or inorganic ammonium;

B) compounds of the formula (II)

$$E\text{---}[\text{AO}]_n\text{---}[\text{BO}]_m\text{---}R^2 \qquad (II)$$

where
E is a phenoxy group or a primary amino group,
A and B independently of one another are an alkylene radical having 2 to 4 C atoms,
(n+m) is 1 to 50, and
R$^2$ is H, an alkyl group having 1 to 8 C atoms, —COOM, —SO$_3$M, —OSO$_3$M, —PO$_3$M$_2$ or —OPO$_3$M$_2$;

C) amino acids; and

D) aliphatic, linear or branched aminosulphonic acids having 2 to 10 C atoms.

3. The water-soluble modified lignin ML according to claim 2, wherein the compound of the formula (I) is an aromatic compound having at least one sulphonic acid group or carboxylic acid group and at least one amino group bonded to the phenylene or naphthylene radical.

4. The water-soluble modified lignin ML according to claim 1, wherein the organic compound V is selected from the group consisting of glycine, alanine, glutamic acid, aspartic acid, tyrosine, serine, histidine and arginine.

5. The water-soluble modified lignin ML according to claim 1, wherein the organic compound V is taurine.

6. The water-soluble modified lignin ML according to claim 1, wherein the enzymatic reaction is carried out using 0.4 to 15 mmol of organic compound V per gram of water-insoluble lignin L.

7. The water-soluble modified lignin ML according to claim 1, wherein in the enzymatic reaction the at least one enzyme is selected from the group consisting of laccases or tyrosinases.

8. The water-soluble modified lignin ML according to claim 1, wherein the enzymatic reaction is carried out in a reaction medium comprising water and optionally at least one organic solvent.

9. The water-soluble modified lignin ML according claim 1, wherein the enzymatic reaction is carried out in the presence of a mediator.

10. A process for preparing the water-soluble modified lignin ML according to claim 1, the process comprising enzymatically reacting a water-insoluble lignin L with at least one organic compound V, the organic compound V possessing at least one selected from the group consisting of a primary amino group, a secondary amino group, a hydroxyl group and a phenyl group and having an average molecular weight $M_n$ in the range from 75 to 2500 g/mol,
wherein in the step of enzymatically reacting the water-insoluble lignin L with the at least one organic compound, at least one enzyme selected from the group consisting of peroxidases and phenol oxidases is present.

11. A reaction product from the process according to claim 10, comprising the water soluble modified lignin ML.

12. A method comprising dispersing the water-soluble modified lignin ML according to claim 1 in a composition comprising mineral binders.

13. A composition comprising
at least one mineral binder,
at least one water-soluble modified lignin ML according to claim 1, and optionally water.

14. A shaped body obtained by setting and curing the composition according to claim 13 after contact thereof with water.

15. A dispersant for mineral binders, comprising at least one water-soluble modified lignin ML according to claim 1.

16. The process for preparing the water-soluble modified lignin ML according to claim 10, wherein the at least one enzyme is selected from the group consisting of laccases and tyrosinases.

* * * * *